US012447034B2

(12) United States Patent
Lotufo

(10) Patent No.: US 12,447,034 B2
(45) Date of Patent: Oct. 21, 2025

(54) WEARABLE PLANTAR FASCIITIS TREATMENT DEVICE AND RELATED SYSTEMS AND METHODS

(71) Applicant: Christopher D. Lotufo, Ooltewah, TN (US)

(72) Inventor: Christopher D. Lotufo, Ooltewah, TN (US)

( * ) Notice: Subject to any disclaimer, the term of this patent is extended or adjusted under 35 U.S.C. 154(b) by 288 days.

(21) Appl. No.: 18/297,689

(22) Filed: Apr. 10, 2023

(65) Prior Publication Data

US 2023/0320881 A1 Oct. 12, 2023

Related U.S. Application Data

(60) Provisional application No. 63/328,769, filed on Apr. 8, 2022.

(51) Int. Cl.
*A61F 5/00* (2006.01)
*A61F 5/01* (2006.01)

(52) U.S. Cl.
CPC ............ *A61F 5/0111* (2013.01); *A61F 5/019* (2013.01)

(58) Field of Classification Search
USPC .............................................. 602/23, 65, 30
See application file for complete search history.

(56) References Cited

U.S. PATENT DOCUMENTS

| | | | | |
|---|---|---|---|---|
| 3,506,000 | A * | 4/1970 | Baker | A61F 13/066 602/65 |
| 5,772,621 | A * | 6/1998 | Unruh | A61F 5/019 602/65 |
| 2016/0100973 | A1* | 4/2016 | Nelson | A61F 5/0127 602/23 |
| 2016/0302953 | A1* | 10/2016 | Amanatullah | A61F 5/0111 |
| 2017/0196737 | A1 | 7/2017 | Riley et al. | |
| 2017/0296370 | A1 | 10/2017 | Riley et al. | |
| 2019/0183209 | A1 | 6/2019 | Wong | |

* cited by examiner

*Primary Examiner* — Kim M Lewis
(74) *Attorney, Agent, or Firm* — Fredrikson & Byron, P.A.

(57) ABSTRACT

Wearable treatment devices and methods for treatment of plantar fasciitis. Certain devices have a heel collar attachable to a heel of a foot and a toe brace having an elongate band attachable to the heel collar and at least one toe loop disposed at a distal end of the elongate band. Some embodiments also include a support strap attachable to the elongate band, the support strap having two strap arms positionable around the heel and attachable to each other.

20 Claims, 12 Drawing Sheets

WEARABLE PLANTAR FASCIITIS TREATMENT DEVICE AND RELATED SYSTEMS AND METHODS

CROSS-REFERENCE TO RELATED APPLICATION(S)

This application claims the benefit under 35 U.S.C. § 119(e) to U.S. Provisional Application 63/328,769 filed Apr. 8, 2022 and entitled "Wearable Plantar Fasciitis Treatment Device and Related Systems and Methods," which is hereby incorporated herein by reference in its entirety.

FIELD

The various embodiments herein relate to plantar fasciitis treatment and, more specifically, to wearable devices for treating plantar fasciitis.

BACKGROUND

Most known wearable devices for treating plantar fasciitis are aimed at preventing pronation. These devices can be split into two categories. The first category of devices limits pronation and reduces strain on the plantar fascia by stretching the calf. Calf-stretching devices falling within this first category include several wearable devices, including night splints, and the Strasburg sock. The second category of devices supports the medial longitudinal arch of the foot in order to limit pronation and reduce strain on the plantar fascia. Devices falling into this second category include arch pads and over-the-counter or custom foot orthotics.

There is a need in the art for an improved wearable device that replicates the function of the plantar fascia.

BRIEF SUMMARY

Discussed herein are various wearable devices for replicating the windlass mechanism created by the plantar fascia. Certain of the device embodiments include at least heel collar and a toe brace. Other implementations include a heel collar, a toe brace, and a support strap.

In Example 1, a wearable treatment device comprises a heel collar attachable to a heel of a foot, and a toe brace comprising an elongate band attachable to the heel collar and at least one toe loop disposed at a distal end of the elongate band.

Example 2 relates to the wearable treatment device according to Example 1, further comprising a support strap attachable to the elongate band, the support strap comprising two strap arms positionable around the heel and attachable to each other.

Example 3 relates to the wearable treatment device according to Example 2, wherein the two strap arms are attached to each other such that the support strap is v-shaped.

Example 4 relates to the wearable treatment device according to Example 1, wherein the heel collar comprises a heel sleeve positionable around the heel of the foot, and a first attachment strap attached at each end to opposite sides of the heel sleeve, wherein the first attachment strap is positionable around a dorsum of the foot.

Example 5 relates to the wearable treatment device according to Example 4, wherein the heel collar further comprises two attachable straps attached to the sleeve, wherein each of the two attachable straps is positionable around the dorsum and attachable to each other.

Example 6 relates to the wearable treatment device according to Example 1, wherein the elongate band is tensionable.

Example 7 relates to the wearable treatment device according to Example 1, wherein the elongate band is tensioned when the at least one toe loop is attached to toe of the foot and a proximal end of the elongate band is attached to the heel collar.

Example 8 relates to the wearable treatment device according to Example 7, wherein the elongate band replicates the action of the windlass mechanism when the elongate band is tensioned.

In Example 9, a wearable treatment device comprises a heel collar attachable to a heel of a foot and a toe brace comprising an elongate band attachable to the heel collar and at least one toe loop disposed at a distal end of the elongate band. The device further comprises a support strap attachable to the elongate band, the support strap comprising two strap arms positionable around the heel and attachable to each other.

Example 10 relates to the wearable treatment device according to Example 9, wherein the heel collar comprises a heel sleeve positionable around the heel of the foot, and a first attachment strap attached at each end to opposite sides of the heel sleeve, wherein the first attachment strap is positionable around a dorsum of the foot.

Example 11 relates to the wearable treatment device according to Example 10, wherein the heel collar further comprises two attachable straps attached to the sleeve, wherein each of the two attachable straps is positionable around the dorsum and attachable to each other.

Example 12 relates to the wearable treatment device according to Example 9, wherein the two strap arms are attached to each other such that the support strap is v-shaped.

Example 13 relates to the wearable treatment device according to Example 9, wherein the elongate band is tensioned when the at least one toe loop is attached to at least one toe of the foot and a proximal end of the elongate band is attached to the heel collar.

Example 14 relates to the wearable treatment device according to Example 13, wherein the elongate band replicates the action of the windlass mechanism when the elongate band is tensioned.

In Example 15, a method of treating plantar fasciitis with a wearable treatment device comprises positioning a heel collar around a heel of a foot, attaching at least one toe loop of a toe brace to at least one toe of the foot, and attaching a proximal end of an elongate band of the toe brace to a portion of the heel collar on a bottom of the foot such that the elongate band is tensioned.

Example 16 relates to the method according to Example 15, further comprising attaching a support strap around the heel such that the support strap is also disposed around a position of the heel collar and the toe brace.

Example 17 relates to the method according to Example 16, wherein the attaching the support strap around the heel further comprises attaching the support strap to the elongate band and attaching opposing ends of the support strap to each other at a back of the heel.

Example 18 relates to the method according to Example 15, wherein the positioning the heel collar around the heel of the foot further comprises positioning a dorsum strap around a dorsum of the foot.

Example 19 relates to the method according to Example 15, further comprising wrapping two attachable straps of the heel collar around the dorsum and attaching the two attachable straps to each other.

Example 20 relates to the method according to Example 15, wherein the attaching the elongate band to the portion of the heel collar such that the elongate band is tensioned replicates the action of the windlass mechanism.

While multiple embodiments are disclosed, still other embodiments will become apparent to those skilled in the art from the following detailed description, which shows and describes illustrative embodiments. As will be realized, the various implementations are capable of modifications in various obvious aspects, all without departing from the spirit and scope thereof. Accordingly, the drawings and detailed description are to be regarded as illustrative in nature and not restrictive.

DETAILED DESCRIPTION

The various embodiments herein relate to a wearable plantar fasciitis treatment device 10 that can be used to provide support to and reduce the stress placed on an inflamed plantar fascia. According to some implementations, the device 10 recreates the function of the plantar fascia by engaging the windlass mechanism, thereby reducing the force placed on the plantar fascia.

Figure 1A:
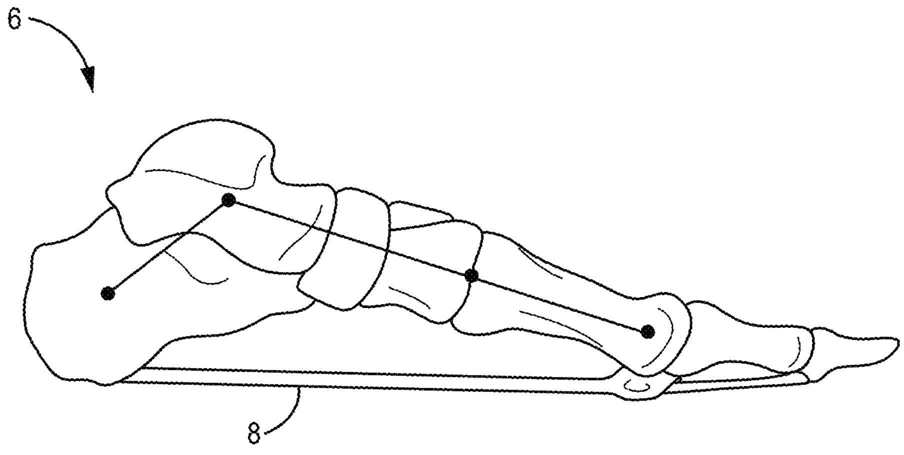
FIG. 1A is a cross-sectional side view of the bones and plantar fascia of a foot in a resting state.
Figure 1B:
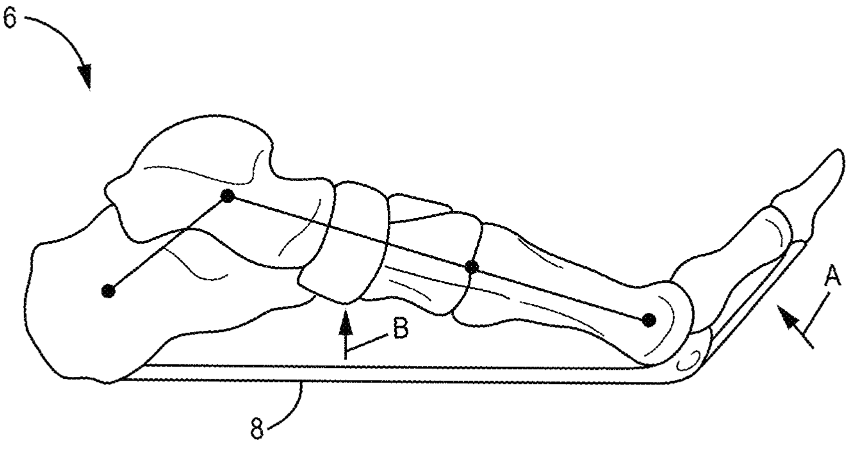
FIG. 1B is a cross-sectional side view of the foot of FIG. 1A while the toes dorsiflex.

The windlass mechanism is a biomechanical feature of the foot that results in stabilizing the arch of the foot. More specifically, as shown in FIGS. 1A and 1B, the mechanism refers to the tensioned attachment of the plantar fascia ligament 8 to the heel bone and the base of the toes. FIG. 1A depicts a foot 6 in a relaxed state. As the toes dorsiflex upon heel rise as represented by arrow A in FIG. 1B, further tension is placed on the plantar fascia 8 that brings the heel bone closer to the toes, accentuating the arch of the foot (as represented by arrow B) and locking the midtarsal joint to ready the foot for push off.

Figure 2A:
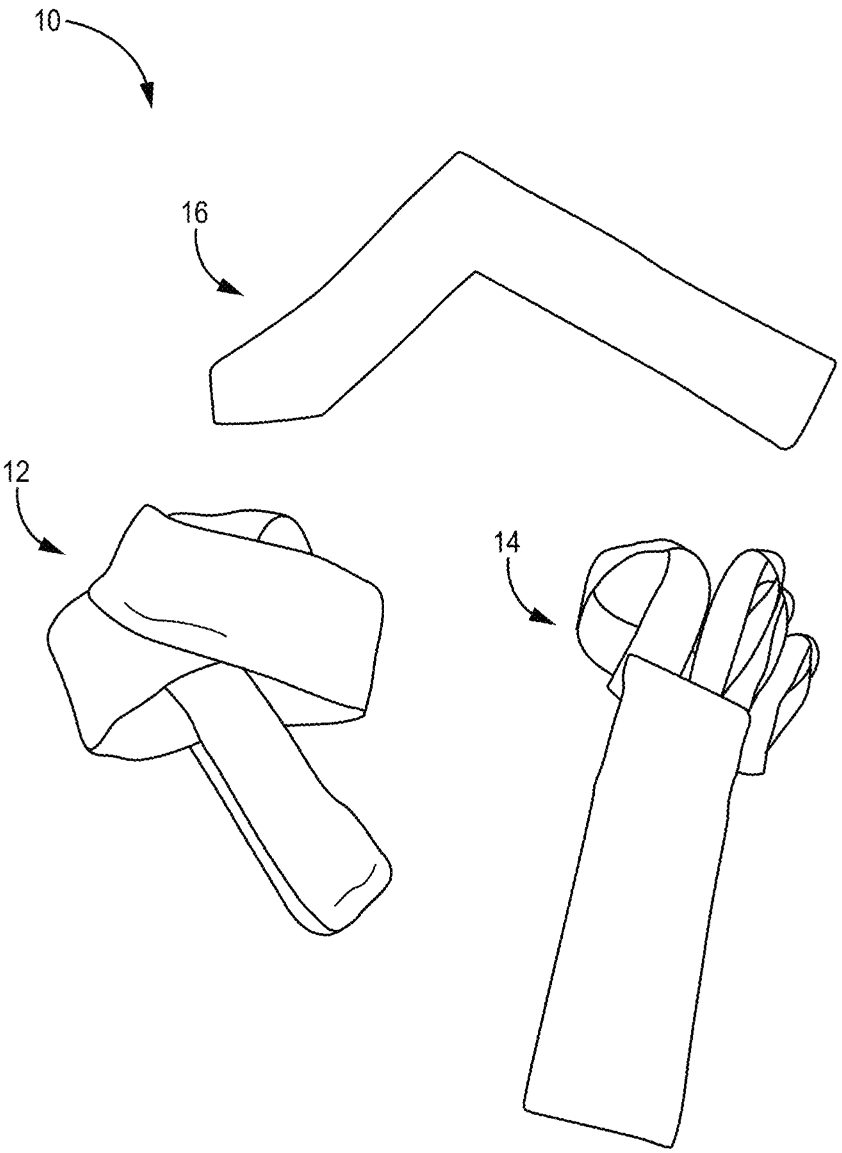
FIG. 2A is a top view of a plantar fasciitis treatment device, including the heel collar, toe brace, and support strap, according to one embodiment.
Figure 2B:
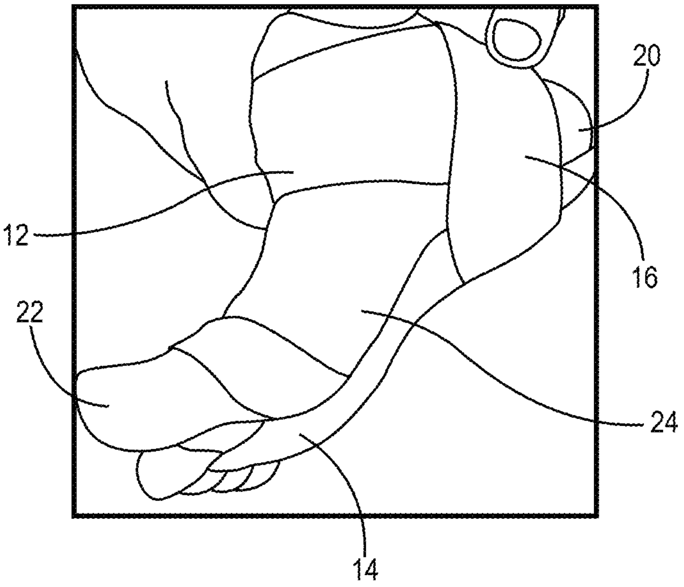
FIG. 2B is perspective view of the treatment device positioned on a user's foot, according to one embodiment.

In one implementation as best shown in FIGS. 2A and 2B, the device 10 has three separate, couplable pieces: a heel collar 12, a toe brace 14, and a support strap 16. According to some implementations and as will be described in additional detail below, each of the three pieces (the collar 12, brace 14, and strap 16) are made of a flexible, elastic material with attachment features at the appropriate locations as described herein. As shown in FIG. 2B, each of the three pieces 12, 14, 16 can be attached to a patient's foot 18, with the heel collar 12 being attached to heel 20, the toe brace 14 being attached to the toes 22 and extended along the plantar surface 24 of the foot 18 (and attached to the collar 12), and the strap 16 attached to the brace 14 and wrapped around the heel 20. The three pieces 12, 14, 16 and the attachment of each to the patient's foot will be described in additional detail below. Alternatively, in certain embodiments, the device 10 can have solely a heel collar 12 and a toe brace 14, with the support strap 16 being an optional piece.

Figure 3A:
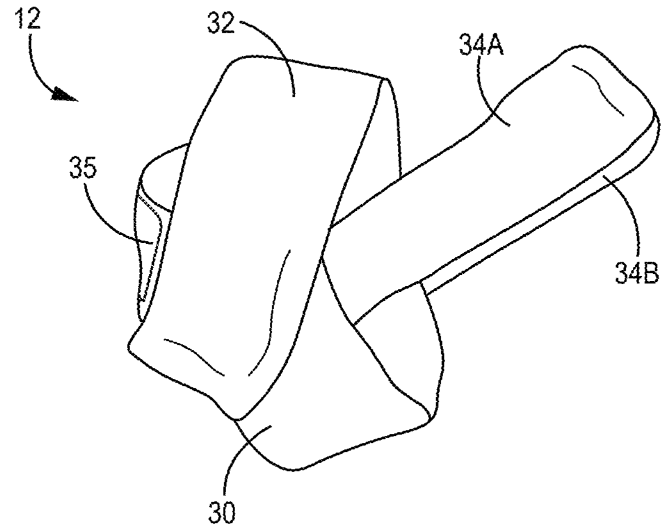
FIG. 3A is a side view of a heel collar, according to one embodiment.
Figure 3B:
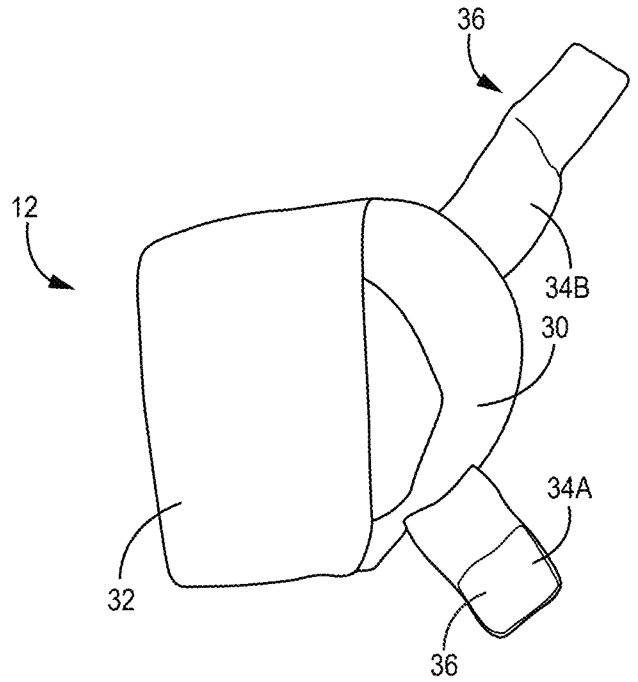
FIG. 3B is a top view of the heel collar of FIG. 3A, according to one embodiment.

As best shown in FIGS. 3A-B, the heel collar 12 has a heel sleeve 30 that is a circular sleeve 30 positionable around the heel 20 of the foot 18, a dorsum strap 32 that is attached at each end to opposite sides of the sleeve 30 and is positionable around the dorsum of the foot 18, and two attachable straps 34A, 34B that are each attached to the sleeve 30 as shown and can be coupled to each other around the dorsum to provide additional attachment and support. Each of the sleeve 30 and strap 32 are elastic such that they can be stretched out while being placed over the target parts of the foot 18 as discussed below. In one implementation, as best shown in FIGS. 3A and 4B, the sleeve 30 has an attachment feature (such as, for example, VELCRO® hook and loop fastener) 35 disposed on an outer surface of the sleeve 30 at a location such that it is positioned under the heel 20 of the foot 18 when the sleeve 30 is placed on the foot 18 as discussed below. Each of the straps 34A, 34B has an attachment feature (such as, for example, VELCRO® hook and loop fastener) 36 at the unattached end such that the two straps 34A, 34B can be attached to each other as described in further detail below. Alternatively, in some implementations, the heel collar 12 has solely the dorsum strap 32 and no attachable straps. In certain versions of the heel collar 12 that do not have attachable straps, the dorsum strap 32 can be wider and cover not only a top portion of the foot but can also extend over a front portion of the ankle/leg.

The various components of the heel collar 12, including the sleeve 30, the dorsum strap 32, and the optional attachable straps 34A, 34B can be made of any durable, flexible material. For example, in one embodiment, the material can be elastic material available from eBoot on Amazon.com. For example, the sleeve 30 and dorsum strap 32 can be made from a length of elastic material from a 2-inch wide spool of elastic material from eBoot. Further, the attachable straps 34A, 34B can be made from a length of elastic material from a 1 inch wide spool of elastic material from eBoot. Alternatively, the components can have any other widths that can be used to achieve the same functionality as described herein can be used. Further, the components can be made from any similar flexible material from any source. In addition, the attachment features 35 (and any other attachment features in any other components of any embodiments herein) can be sew-on hook and loop tape fastener from Lakestory on Amazon.com.

Figure 4A:
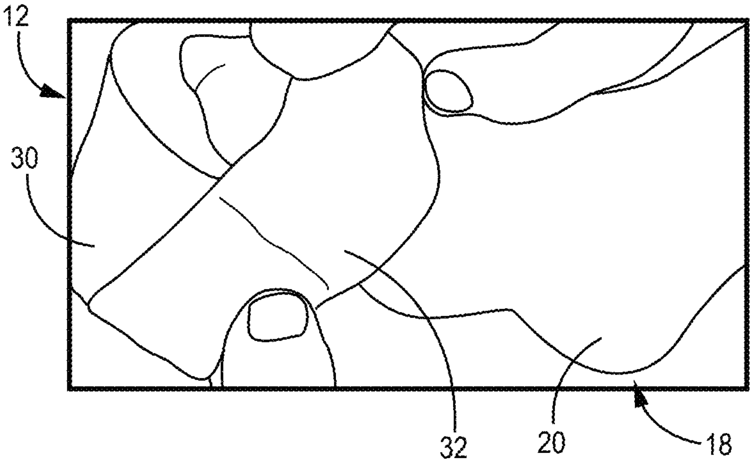
FIG. 4A is a perspective view of a heel collar being placed on a user's foot, according to one embodiment.
Figure 4B:
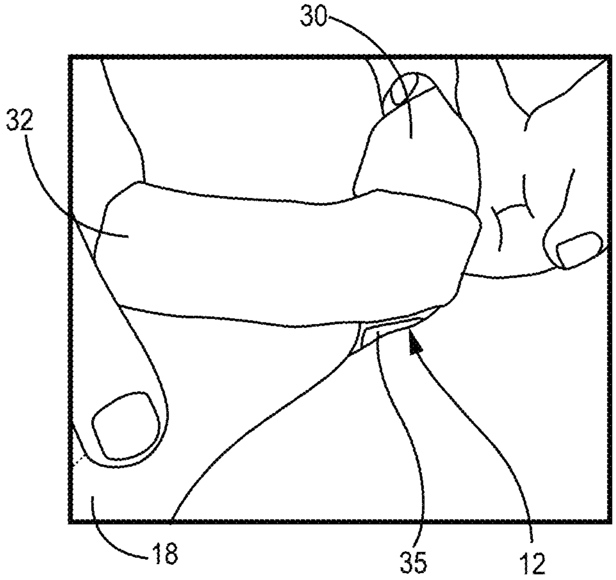
FIG. 4B is a perspective view of the heel collar of FIG. 4A being positioned on the heel of the user's foot, according to one embodiment.
Figure 4C:
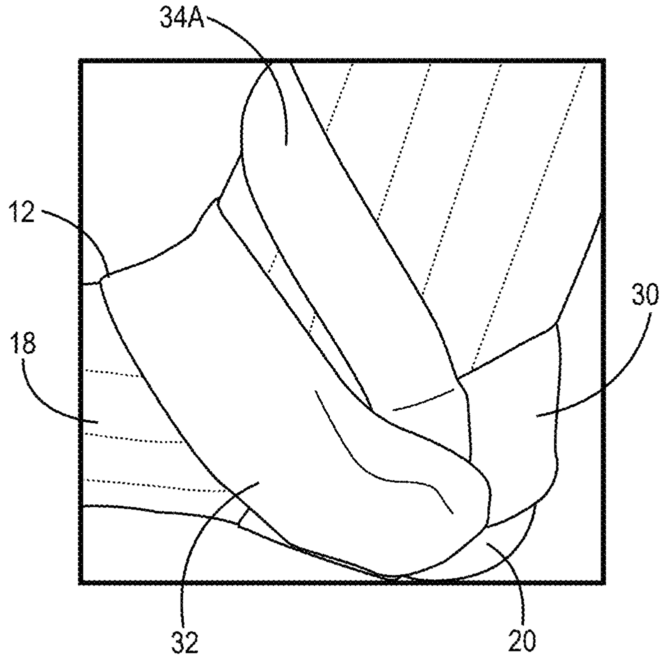
FIG. 4C is a perspective view of the heel collar of FIG. 4A attached to the user's foot, according to one embodiment.

In use, as best shown in FIGS. 4A-4C, the heel collar 12 can be attached in the following manner, according to one embodiment. First, the foot 18 is inserted through the dorsum strap 32 as shown in FIG. 4A and the collar 12 is urged over the foot 18 toward the heel 20. Once the collar 12 reaches the heel 20, as best shown in FIG. 4B, the dorsum strap 32 is positioned over the dorsum and the heel sleeve 30 can be positioned over the heel 20. As best shown in FIG. 4C, once the heel sleeve 30 is positioned as desired around the heel 20, the two optional attachable straps 34A, 34B are extended around the dorsum from opposite sides of the foot 18 and attached to each other at the dorsum (and adjacent to the dorsum strap 32 as shown) via the attachment features (discussed above) as shown, thereby providing further attachment for the heel collar 12.

Figure 5A:
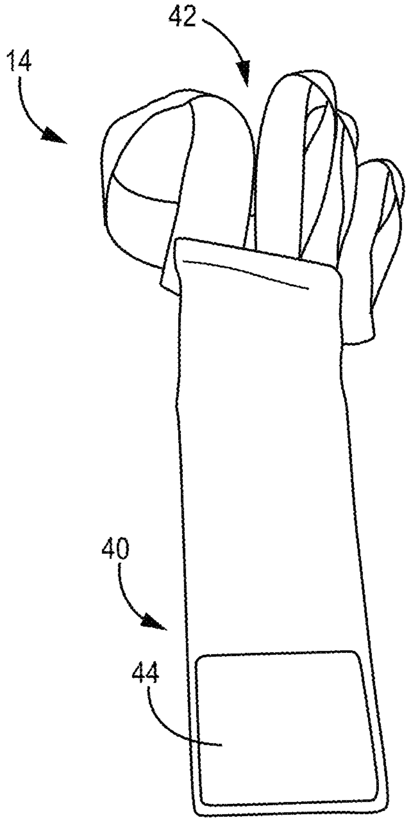
FIG. 5A is a top view of a toe brace, according to one embodiment.
Figure 5B:
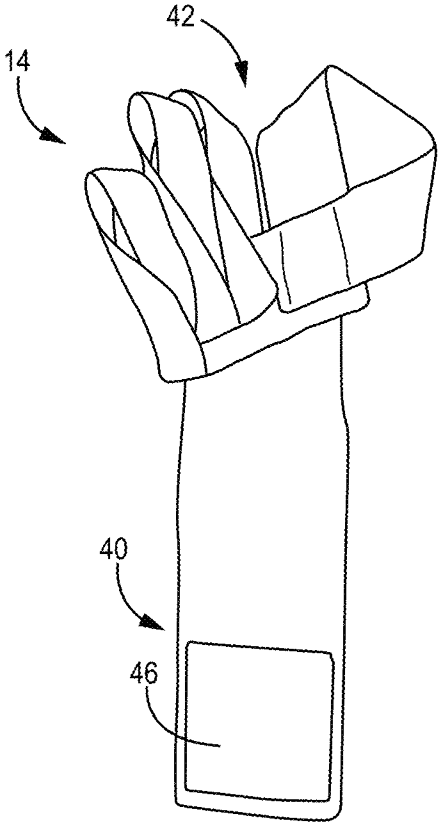
FIG. 5B is a bottom view of the toe brace of FIG. 5A, according to one embodiment.

As best shown in FIGS. 5A and 5B, the toe brace 14 has an elongate band 40 with a set of toe loops 42 attached at a distal end of the band 40. In the exemplary embodiment shown, the brace 14 has four toe loops 42—one for the big toe and three for the three adjacent toes. Alternatively, the brace 14 can have one toe loop, two toe loops, three toe loops, or five toe loops. In those embodiments with one toe loop 42, the toe loop 42 is configured to be positioned around the big toe. The band 40 is made of an elastic material. In addition, the loop/loops 42 can be made of an elastic material, resulting in the loops 42 being expandable (and retractable to their original size) such that the user's/patient's toes can fit through the one or more loops 42 (via the expansion of the loops) and the one or more loops 42 are disposed around the one or more toes with some tension (via the retraction), thereby ensuring that the loops 42 are maintained in the desired positions on the toes. FIG. 5A provides a top view of the brace 14, while FIG. 5B provides an underside view. The top of the brace 14 is the side that is placed into contact with the underside of the foot 18, as discussed below. Further, the band 40 can have an attachment feature (such as, for example, VELCRO® hook and loop fastener) 44 on the top side of the brace 14 as best shown in FIG. 5A for attachment to the heel sleeve 30 as discussed below. Alternatively, certain versions of the band 40 can have no attachment feature on the top side of the band 40 as will be mentioned below. In addition, the band 40 can also have an attachment feature (such as, for example, VELCRO® hook and loop fastener) 46 on the underside of the brace 14 as best shown in FIG. 5B for attachment of the support strap 16 as discussed below. In certain alternative embodiments (including, for example, those embodiments in which the heel collar 12 has no attachable straps and/or those embodiments in which no support strap is used), the toe brace 14 can also have optional attachable straps attached to the proximal end of the band 40 that can be similar to and operate in a fashion similar to either or both of the attachment straps 34A, 34B of the heel collar 12 or the support strap 16 as described herein.

The various components of the toe brace 14, including the elongate band 40 and toe loops 42, can be made of any durable, flexible material. For example, in one embodiment, the material can be elastic material available from eBoot on Amazon.com. For example, the elongate band 40 can be made from a length of elastic material from a 2-inch wide spool of elastic material from eBoot. Further, the toe loops 42 can be made from a length of elastic material from a 0.6 or 1 inch wide spool of elastic material from eBoot. Alternatively, the components can have any other widths that can be used to achieve the same functionality as described herein can be used. Further, the components can be made from any similar flexible material from any source. In addition, the attachment features 44, 46 (and any other attachment features in any other components of any embodiments herein) can be sew-on hook and loop tape fastener from Lakestory on Amazon.com.

Figure 6A:
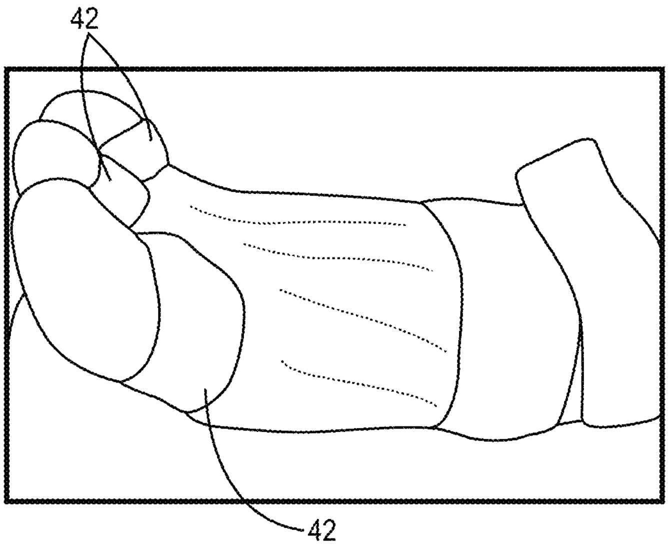
FIG. 6A is a perspective top view of a toe brace positioned on a user's foot, according to one embodiment.
Figure 6B:
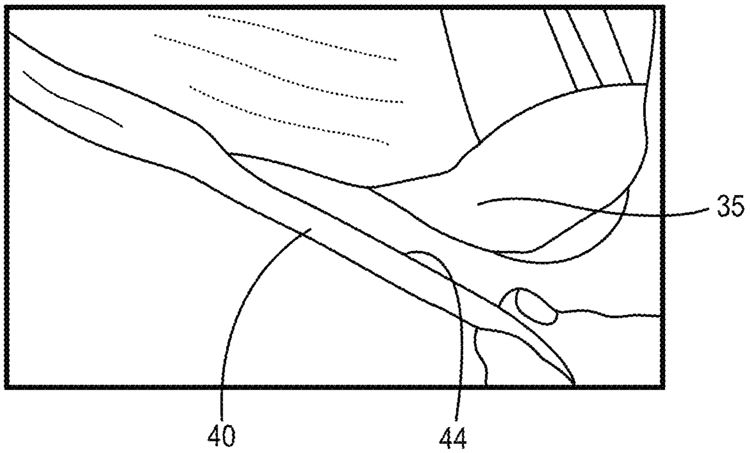
FIG. 6B is a perspective bottom view of the toe brace of FIG. 6A being attached to the heel collar on the user's foot, according to one embodiment.

In use, as best shown in FIGS. 6A and 6B, the toe brace 14 is attached in the following manner, according to certain implementations. First, the toe loops 42 are placed around the target toes as best shown in FIG. 6A (with the loop 42 being placed around the big toe in those embodiments having only a single toe loop 42, as mentioned above). Once the toes are positioned within the loops 42, as best shown in FIG. 6B, the band 40 is extended along the plantar surface of the foot 18 and stretched proximally with a desired amount of force and the attachment feature 44 is used to attach the top surface of the band 40 to the attachment feature 35 of the heel sleeve 30 such that the desired amount of tension in the band 40 is retained as a result of the attachment. Alternatively, in those embodiments without the attachment feature on the top of the band 40, the band 40 is not attached to the heel sleeve 30. Instead, the support strap 16 as discussed below is wrapped around the band 40 and the heel sleeve 30 as discussed below such that the support strap 16 helps to keep the band 40 in place.

Figure 7:
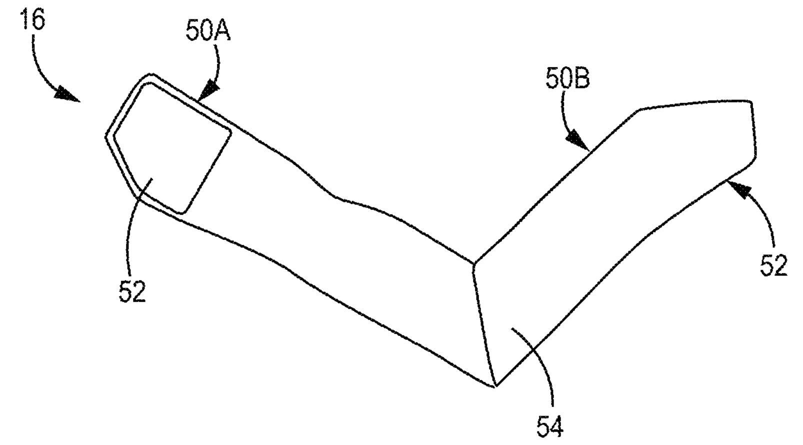
FIG. 7 is a plan view of a support strap, according to one embodiment.

As best shown in FIG. 7, the support strap 16 has two elongate strap arms 50A, 50B attached to each other at an end of each arm 50A, 50B such that the two arms 50A, 50B form a V shape. The strap 16 has an attachment feature (such as, for example, VELCRO® hook and loop fastener) 52 at each unattached end of the arms 50A, 50B and an attachment feature (such as, for example, VELCRO® hook and loop fastener) 54 at the connection of the two arms 50A, 50B.

According to various embodiments, the support strap 16 is made of a flexible, non-elastic material that is conformable (around the foot and heel) but doesn't stretch. In addition, the attachment features 52, 54 (and any other attachment features in any other components of any embodiments herein) can be sew-on hook and loop tape fastener from Lakestory on Amazon.com.

Figure 8A:
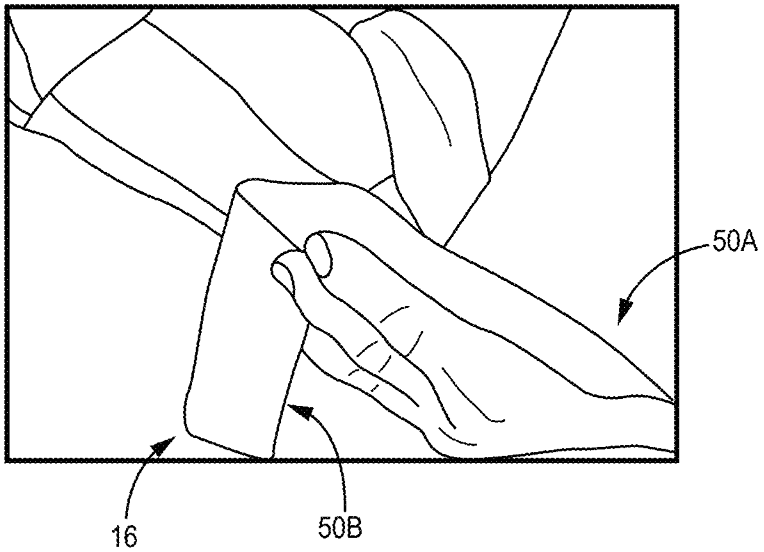
FIG. 8A is a perspective bottom view of a support strap being attached to a toe brace on a user's foot, according to one embodiment.
Figure 8B:
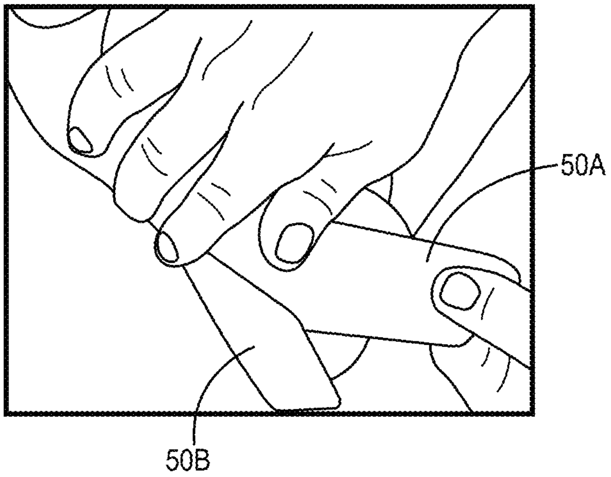
FIG. 8B is a perspective bottom view of the support strap of FIG. 8A being wrapped around the heel of the user's foot, according to one embodiment.

In use, as best shown in FIGS. 8A-8B, the support strap 16 is attached in the following manner, according to one embodiment. First, the attachment feature 54 is positioned against and attached to the attachment feature 46 on the underside of the band 40 (which is positioned under the foot after being attached thereto as shown in FIG. 5B) as best shown in FIG. 8A. Each of the arms 50A, 50B is then wrapped around the heel 20 and attached to each other at the attachment features 52 at the back of the foot 18 as best shown in FIGS. 8B and 9A.

Figure 9A:
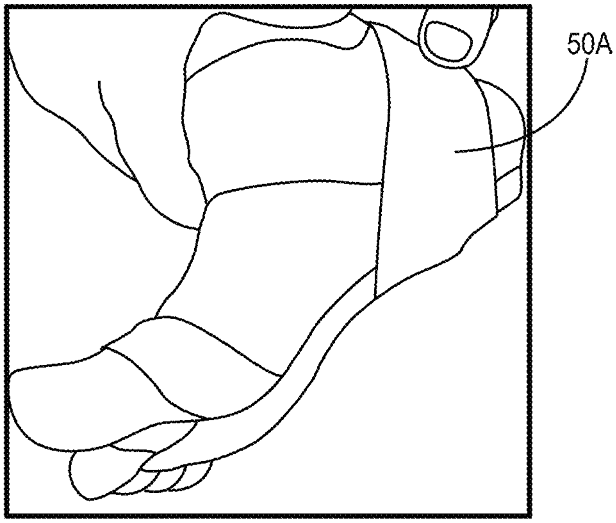
FIG. 9A is a perspective bottom view of a plantar fasciitis treatment device attached to a user's foot, according to one embodiment.
Figure 9B:
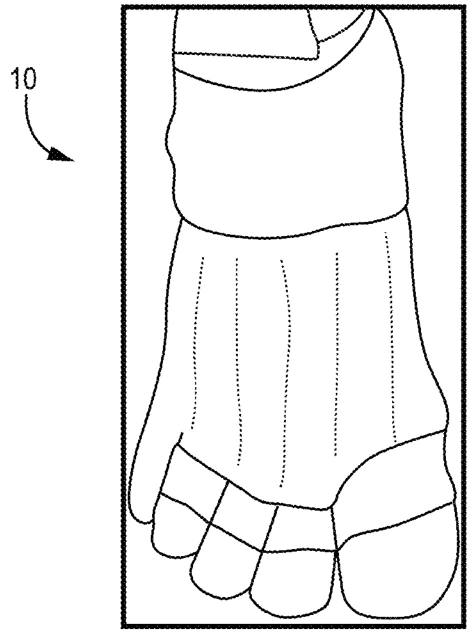
FIG. 9B is a perspective top view of the plantar fasciitis treatment device of FIG. 9A attached to the user's foot, according to one embodiment.
Figure 9C:
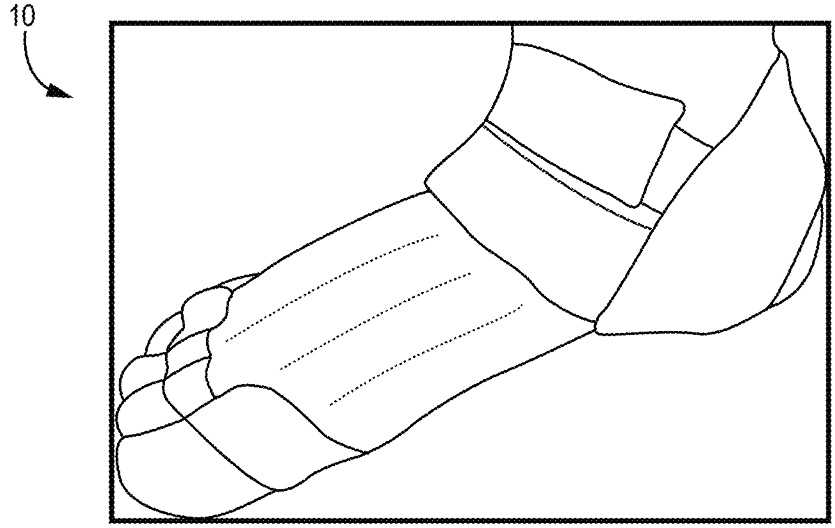
FIG. 9C is a perspective side view of the plantar fasciitis treatment device of FIG. 9A attached to the user's foot, according to one embodiment.

Once the three separate pieces 12, 14, 16 are attached as described above, the resulting treatment device 10 is shown in FIGS. 9A-9C. In use, the device 10 can be worn by a patient under or over the patient's sock. Further, in certain embodiments, a shoe (not shown) can be placed over the device 10 such that the device 10 can be worn all day within the shoe.

The attachment of the toe brace 14 to the toes at one end and to the heel collar 12 at the other end as described above helps to create an artificial windlass mechanism, thereby providing support to an inflamed plantar fascia and reduce the stress placed thereon. More specifically, the toe brace 14 (in combination with the heel collar 12 and the support strap 16) replicate the windlass mechanism as a result of the elongate band 40 being attached to and extending from the toes to the heel (as best shown in FIGS. 2B and 9A) and establishing a tension therebetween in a fashion similar to the plantar fascia ligament.

Figure 10:
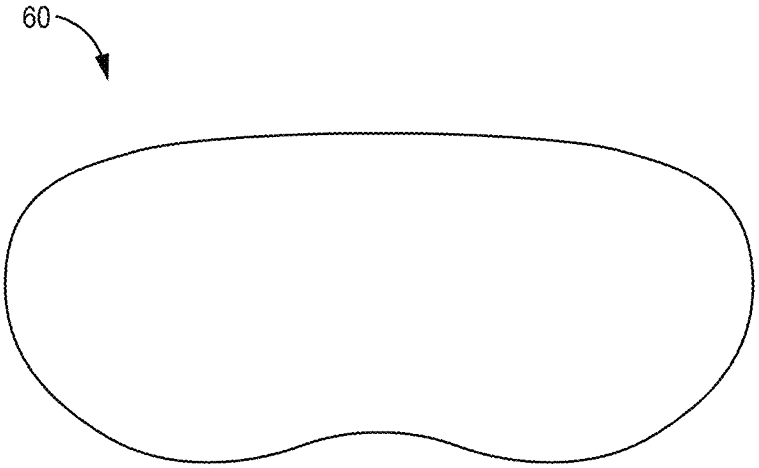
FIG. 10 is a plan view of a heel pad, according to one embodiment.

According to some alternative implementations, the device 10 can also have a heel pad 60 as shown in FIG. 10 that can be permanently or removably attached to the heel sleeve 30, and more specifically to the portion of the heel sleeve 30 disposed on the back portion of the heel. The heel pad 60 provides additional cushion for the patient's heel while enhancing the grip of the heel sleeve 30 on the patient's heel. In one specific embodiment, the pad 60 is attached to back of the heel sleeve 30 such that the pad 60 helps to prevent slippage of the heel sleeve 30 as the windlass mechanism is engaged by the device 10. According to one exemplary implementation, the pad 60 is a Dr. Foot Heel Grip available from Dr. Foot on Amazon.com. Alternatively, the heel pad 60 can be any commercially available heel pad.

In certain additional alternative embodiments, an optional arch support component (not shown) can be provided with the toe brace 14. More specifically, the arch support can be attached to or integral with the band 40 or can be a separate piece that is positioned between the plantar aspect of the patient's foot 18 and the band 40. The arch support component can be any know arch support component that is commercially available.

While the various systems described above are separate implementations, any of the individual components, mechanisms, or devices, and related features and functionality, within the various system embodiments described in detail above can be incorporated into any of the other system embodiments herein.

The terms "about" and "substantially," as used herein, refers to variation that can occur (including in numerical quantity or structure), for example, through typical measuring techniques and equipment, with respect to any quantifiable variable, including, but not limited to, mass, volume, time, distance, wave length, frequency, voltage, current, and electromagnetic field. Further, there is certain inadvertent error and variation in the real world that is likely through differences in the manufacture, source, or precision of the components used to make the various components or carry out the methods and the like. The terms "about" and "substantially" also encompass these variations. The term "about" and "substantially" can include any variation of 5% or 10%, or any amount—including any integer—between 0% and 10%. Further, whether or not modified by the term "about" or "substantially," the claims include equivalents to the quantities or amounts.

Numeric ranges recited within the specification are inclusive of the numbers defining the range and include each integer within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾This applies regardless of the breadth of the range. Although the various embodiments have been described with reference to preferred implementations, persons skilled in the art will recognize that changes may be made in form and detail without departing from the spirit and scope thereof.

Although the various embodiments have been described with reference to preferred implementations, persons skilled in the art will recognize that changes may be made in form and detail without departing from the spirit and scope thereof.

What is claimed is:

1. A wearable treatment device comprising:
(a) a heel collar attachable to a heel of a foot, the heel collar comprising:
(i) a heel sleeve positionable around the heel of the foot; and
ii) a first attachment strap attached at each end to opposite sides of the heel sleeve, wherein the first attachment strap is positionable around a dorsum of the foot;
(b) a toe brace comprising:
(i) an elongate band attachable to the heel collar; and
(ii) At least one toe loop disposed at a distal end of the elongate band;
(c) a v-shaped support strap attachable to the elongate band, the support strap comprising two strap arms positionable around the heel and attachable to each other.

2. The wearable treatment device of claim 1, wherein the two strap arms are attached to each other such that the support strap is v-shaped.

3. The device of claim 1, wherein the heel collar further comprises two attachable straps attached to the sleeve, wherein each of the two attachable straps is positionable around the dorsum and attachable to each other.

4. The device of claim 1, wherein the elongate band is tensionable.

5. The device of claim 1, wherein the elongate band is tensioned when the at least one toe loop is attached to a toe of the foot and a proximal end of the elongate band is attached to the heel collar.

6. The device of claim 5, wherein the elongate band replicates the action of the windlass mechanism when the elongate band is tensioned.

7. A wearable treatment device comprising:
(a) a heel collar attachable to a heel of a foot, the heel collar comprising:
(i) a heel sleeve positionable around the heel of the foot; and (ii) a first attachment strap attached at each end to opposite sides of the heel sleeve, wherein the first attachment strap is positionable around a dorsum of the foot;

(b) a toe brace comprising:

(i) an elongate band attachable to the heel collar; and (ii) at least one toe loop disposed at a distal end of the elongate band; and (c) a support strap attachable to the elongate band, the support strap comprising two strap arms positionable around the heel and attachable to each other.

8. The device of claim 7, wherein the heel collar further comprises two attachable straps attached to the sleeve, wherein each of the two attachable straps is positionable around the dorsum and attachable to each other.

9. The wearable treatment device of claim 7, wherein the two strap arms are attached to each other such that the support strap is v-shaped.

10. The device of claim 7, wherein the elongate band is tensioned when the at least one toe loop is attached to at least one toe of the foot and a proximal end of the elongate band is attached to the heel collar.

11. The device of claim 10, wherein the elongate band replicates the action of the windlass mechanism when the elongate band is tensioned.

12. The wearable treatment device of claim 7, wherein the at least one toe loop comprises four toe loops.

13. The wearable treatment device of claim 7, wherein the elongate band comprises:

(a) a first attachment feature disposed on a first side of the elongate band, wherein the first attachment feature is coupleable with the heel sleeve; and (b) a second attachment feature disposed on a second side of the elongate band, wherein the second attachment feature is coupleable with the support strap.

14. The wearable treatment device of claim 7, wherein each of the two strap arms comprises an attachment feature disposed near an end of the strap arm, wherein the two strap arms are attachable to each other via the attachment features.

15. The wearable treatment device of claim 8, wherein each of the two attachment straps comprises an attachment feature disposed near an end of the attachment strap, wherein the two attachment straps are attachable to each other via the attachment features.

16. A method of treating plantar fasciitis with a wearable treatment device, the method comprising:

positioning a heel collar around a heel of a foot;

attaching at least one toe loop of a toe brace to at least one toe of the foot; and attaching a proximal end of an elongate band of the toe brace to a portion of the heel collar on a bottom of the foot such that the elongate band is tensioned; and attaching a support strap around the heel such that the support strap is also disposed around a position of the heel collar and the toe brace.

17. The method of claim 16, wherein the attaching the support strap around the heel further comprises attaching the support strap to the elongate band and attaching opposing ends of the support strap to each other at a back of the heel.

18. The method of claim 16, wherein the positioning the heel collar around the heel of the foot further comprises positioning a dorsum strap around a dorsum of the foot.

19. The method of claim 16, further comprising wrapping two attachable straps of the heel collar around a dorsum of the foot and attaching the two attachable straps to each other.

20. The method of claim 16, wherein the attaching the elongate band to the portion of the heel collar such that the elongate band is tensioned replicates the action of the windlass mechanism.

* * * * *